US005962227A

United States Patent [19]
Hedrick et al.

[11] Patent Number: 5,962,227
[45] Date of Patent: *Oct. 5, 1999

[54] DNA-BASED DIAGNOSTIC TEST FOR DETECTING MYXOBOLUS, THE CAUSE OF SALMONID WHIRLING DISEASE

[75] Inventors: Ronald P. Hedrick; Karl B. Andree; Dolores B. Antonio, all of Davis, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/899,371

[22] Filed: Jul. 23, 1997

Related U.S. Application Data

[60] Provisional application No. 60/022,734, Jul. 26, 1996.
[51] Int. Cl.$^6$ .............................. C12Q 1/68; C07H 21/02
[52] U.S. Cl. ............................................... 435/6; 536/23.1
[58] Field of Search ............................. 435/6, 91.1, 91.2, 435/183, 810; 436/94; 536/23.1, 24.3, 24.33, 25.3; 935/1, 8, 10, 76, 77

[56] References Cited

FOREIGN PATENT DOCUMENTS 8803957  6/1988  WIPO .

OTHER PUBLICATIONS

Hendrick et al., "Three Myxosporeans Found in the Central and Brachial Tissues of Rainbow Trout in California," Journal of Aquatic Animal Health, vol. 3, pp. 55–62, 1991.
Andree et al., "Small Subunit Ribosomal RNA Sequences Unite Alternate Actinosporean and Myxosporean Stages of Myxobolus cerebralis the Causative Agent of Whriing Disease in Salmonid Fish," Journal of Eukaruotic Microbiology, vol. 44, Issue 3, pp. 208–215, May 1997.
Sommer and Tautz, "Minimal homology requirements for PCR primers," Nucleic Acids Research, vol. 17, No. 16, p. 6749, 1989.
Research Genetics "Designer PCR," (advertisement) Nucleic Acids Research vol. 22, No. 15, Aug. 1994.

*Primary Examiner*—Eggerton A. Campbell
*Attorney, Agent, or Firm*—Townsend and Townsend and Crew LLP

[57] ABSTRACT

Compositions, methods and kits directed to detection of the myxozoan parasite Myxobolus spp., for example, *M. cerebralis*. The method comprises contacting an aquatic sample with a nucleic acid comprising a nucleic acid segment capable of selectively hybridizing to the 18S ribosomal nucleic acids of *Myxobolus cerebralis* to form a hybridization complex. Detection of the hybridization complexes indicates the presence of *Myxobolus cerebralis* in the sample.

31 Claims, No Drawings

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 1613 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 1..1613
      (D) OTHER INFORMATION: /note= "18S rRNA gene of Myxobolus cerebralis"

(xi) SEQUENCE DESCRIPTION: SEQ ID NO:1:

```
TATCATCTAT TTGATTGTCT ACCCATTGGA TAACCNNGGG AAATCTAGAG CTAATACATG      60

CAGTTTTGGG CAGCGTTAAA ACTGTCTCAC GGCATTTATT GGACTAAACC AACTACCGTT     120

GCATTGGTTT ACGCTGATGT AGCGAGTAAG GTGAATCTAG ATAACTTTTC TGATCGTATG     180

GCCTATAGCC GGCCACGTTT CAATTGAATT TCTGCCCTAT TAACTAGTTG GTAGTATAGA     240

AGCCTACCAA GGTTGCGATG GGTAACGGGG AATCAGGGTT CGATTCCGGA GAGGGAGCCT     300

GAGAAACGGC TACCACATCC ATGGAAGGCA GCAGGCGCGC AAATTACCCA ATCCAGACAC     360

TGGGAGGTGG TGACGAGAAG TACTAAGTGG TGGCCCTTAG GGTCGCCAGC TTGGAATGGA     420

CGTAATTTAA GTAATTCGAT GAGTAACAAC TGGAGGGCAA GTCTGGTGCC AGCAGCCGCG     480

GTAATTCCAG CTCCAGTAGC GTATTTTAAA GTTGCTGCGT TTAAAACGCT CGTAGTTGGA     540

TCACGCAGTG TAAGTTGGTA GGCTGATCGA ATGGTGCTAC TAACTGCTCC AGCGTTGAAT     600

TTCAAATTCA GTGTTGGAGT AGTGTGCCGT CTTTCAGTTA TTCGCCAATT TACACTACTT     660

ACGCGTAAGG ATGGCAGTTG CCTTTAGTGC GTCGATTGCC GTGTCTTACG GAGTGTGCCT     720

TGAATAAATC AGAGTGCTCA AAGCAGGCTT TTGCTTGAAT GTTAATAGCA TGGAACGAAN     780

AATTGTGTAG TAGTGTGTTG TGACAAATAG CGATCGGTCT TTGACTGAAT GTTATTCAGT     840

TACAGCATAC AGCACCAACC ACCAATAACG GATGTTGGTT CCGTATTGGG GTGATGATTA     900

AAAGGAGCGG TTGGGGGCAT TGGTATTTGG CCGCGAGAGG TGAAATTCTT AGACCGGCCA     960

AGGACTAACG AATGCGAAGG CATTTGCCCA GACCGCCTCG CTTAATCAAG AACGATAGTG    1020

GAGGTTCGAA GACGATCAGA TACCGTCCTA GTTCCCACTG TAAACTATGC CGACCCGGGA    1080

TCAGCATGAA GCTCTTTATA CGCTTTATGT TGGTCCCCCT GGGAAACCTC AAGTTTTTCG    1140

GTTACGGGGA GAGTATGGTC ACAAGGCTGA AACTTAAAGG AATTGACGGA AGGGCACCAC    1200

CAGGAGTGGA GCCTGCGGCT TAATTTGACT CAACACGGGA AAACTTACCA GGTCCGGACA    1260

TCAATAGGAT AGACAAGACT GATAGATCTT TCTTGATATG ATGGATAGTG GTGCATGGCC    1320
```

```
GTTCTTAGTT CGTGGAGTGA TCTGTCAGGC TAATCCCGGT AACGAACGAG ATCTTATTCT       1380

CCATTTGATG AGCGGAAGAA GATAGTGTAG CTCGATGATT GTTTCGGCGA TTCTCAAGTT       1440

ATTCTATCGT AGGCAGTGTT TGTGAATTTA GTGTGAAAAT ACAGTTTGTT GCGAGGACGG       1500

GATAAAACTC TTACTTGTTG CAAATTGTAC TACACCTGAG TTTGTTGGCA TTCCCTTCCG       1560

TTATACGCTG TTCAACTACC CAGTTGAGCA GTGTGTCATG GAGAGACTGT GAG             1613

(2) INFORMATION FOR SEQ ID NO:2:

(i) SEQUENCE CHARACTERISTICS:
        (A) LENGTH: 1608 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1608
        (D) OTHER INFORMATION: /note= "18S rRNA gene of Myxobolus
            insidiosus"

(xi) SEQUENCE DESCRIPTION: SEQ ID NO:2:

TATCATCTAT TTGATTGTCT ACCCATTGGA TAACCGTGGG AAATCTAGAG CTAATACATG        60

CAGCTTGGGA TAGCGTAAGT TGTCTCACGG CATTTATTGG ACAAAACCAA CTACCGACGT       120

AGCAGTTTGC TGTTGCGACG CGTAAGGTGA ATCTAGATAA CTTTGCTGAT CGTATTGGCC       180

TAGTGCCGGC GACGTTTCAA TTGAATTTCT GCCCTATTAA CTTGTTGGTA GTATAGTTGC       240

CTACCAAGGT TCCGACGGGT GACGGGGAAT CAGGGTTCGA TTCCGGAGAG GGAGCCTGAA       300

AAACGGCTAC CACATCCATG GAAGGCAGCA GGCGCCCAAA TTACCCAATC CAGACACCGG       360

GAGGTGGTGA CGAGAAGTAC TAAGTGGTGG CCCTTAGGGT CGCTAGCTTG GAATGGACGT       420

AATTTAAGTA ATTCGATGAG TAACAACTGG AGGGCAAGTC TGGTGCCAGC AGCCGCGGTA       480

ATTCCAGCTC CAGTAGCGTA TTTTAAAGTT GCTGCGTTTA AAACGCTCGT AGTTGGATCA       540

CGCAGTGTAA GTTGGTAAGC TGATTGAATG GTGCTCCAAC TGTTTCGGTG ATAAATTTCT       600

ATTTATTACT AAAACAGTGT GCCTTCTTTC AGTTATTCGC CAATTTACAC TACTTACGCG       660

TAAGGATGGC AGTTGACCTT TAGTGCGTCG ATTGCCGTGT CTTACGGAGT GTGCCTTGAA       720

TAAATCAGAG TGCTCAAAGC AGGCTTTTGC TTGAATGTTA ATAGCATGGA ACGAACAATT       780

GTGTAGTAGT ATGTTGTGAC ACATAGCGAT CGGTCTTTGA CTGAATGCTA TTGCTGTTGC       840

AGCATACAGC ACCAACCACC AATAACGGAT GTTGGTTCCG TATTGGGGTG ATAATTAAAA       900

GGAGCGGTTG GGGGCATTGG TATTTGGCCG CGAGAGGTGA AATTCTTAGA CCGGCCAAGG       960

ACTAACGAAT GCGAAGGCAT TGTCCTAGAC CCCCTCGCTT AATCAAGAAC GATAGTGGGA      1020

GGTTCGAAGA CGAACAGATA CCGTCCTAGT TCCCACTGTA AACTATGCCG ACCCAGGATC      1080

AGCATCGAAG CTCTATATAT GCTTGATGTT GGTCCCCCTG GGAAACCTCA AGTTTTTCGG      1140

TTACGGGGAG AGTATGGTCG CAAGGCTGAA ACTTAAAGGA ATTGACGGAA GGGCACCACC      1200

AGGAGTGGAG CCTGCGGCTT AATTTGACTC AACACGGGAA AACTTACCAG GTCCGGACAT      1260

CAATAGGATA GACAGACTGA TAGATCTTTC TTGATATGAT GGATAGTGGT GCATGGCCGT      1320

TCTTAGTTCG TGGAGTGATC TGTCAGGCTA ATCCCGGTAA CGAACGAGAT CTTATTCTCC      1380

ATTTGATGAG CGGAAGCAGA TGGTGGCTTG AAATTGTCTC GATGAAATTC AAGTTATCAT      1440

CGAAGGCAGT GTTTTCGAGT TTATTGTTGA AATATAAAGA GTTGCGAGAA CGGTCTTACC      1500
```

```
CCCATATCTG GTAGCAATTG GTACTAAATG TAAATTTGTT GGCATTCCCT TCCTTAATAA      1560

CTGTTCTACT TRCCAAAGTG GAGCAGTGTG TCATGGAGAG ACTGTGAG                  1608
```

(2) INFORMATION FOR SEQ ID NO:3:

(i) SEQUENCE CHARACTERISTICS:
        (A) LENGTH: 1606 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1606
        (D) OTHER INFORMATION: /note= "18S rRNA gene of Myxobolus
            squamalis"

(xi) SEQUENCE DESCRIPTION: SEQ ID NO:3:

```
TATAATCTAT TTGATTGTAC AGCCCAATGG ATAACCGCGG GAAATCTAGA GCTAATACAT       60

GCCACCAGTT TGGGAGCGTC AAAACTCTCA AGGCATTTAT TAGACTAATA CCAACTGTAT      120

TTTCAAGGGT AAAACCTTGG AGGTACAAGG TGAATCTAGA TAACTTTGCC GATCGTATGG      180

CTTCGGGCCG GCGACGTTTC AATTGAATTT CTGCCCTATC AACTTGTTGG TAAGGTAGTT      240

GCTTACCAAG GTTGCGACGG GTAACGGGGG ATCAGGGTTC GCTTCCGGAG AGGGAGCCTG      300

AGAAATGGCT ACCACATCCA AGGACGGGAG CAGGCGCGCA TATTACCCAC TCCAGACACT      360

GGGAGGGGGG GGACGAGAAA CTACTCAGTT TTTATTTGGT GGCGGATCTT GGATGGGAGC      420

AATTAAGGCA ATCGATGAGT AACACTGGAG GGCAATTTAG TGCCAGCAGC CGCGGTAATT      480

TCTAGCTCCA GTGGTGTATT TTAATGTTGC TGCGTTTAAA ACGCTCGTAG TTGGATTACG      540

CAGTGCGAGT CGGCAATTAG CAGGGCTTCA CCATAAAAAC TAAGGCGTTT GTTTTGTGAA      600

CATGGATTCC TTGAACGCTA ACAACGTCT TGGTGTGTTG CATGTTGATT ATYTCGCCGG      660

CCCGCACTAC TTGTACGTAA GGATGGCGGT TGACCTTTAG TGCGTTGACT GATCGTGTCT      720

TACGGAGTGT GCCTTGAATA AATCAGAGTG CTCAAAGCAG GCTTACGCTT GAATGTTAAT      780

AGCATGGAAC GAACAATTGT GTAAAAGTGA CTGTACTTAC AATTTGGTGG ATTTATTTGT      840

CAGGTTGTGG GTGCAGTTTA CATCACCAAC CGCCAATAAC GGATGTTGGT TTCCGTATTG      900

GGGTGATGAT TAAAAGGAGC GATTGGGGGC ATTGGTATTT GGCCGCGAGA GGTGAAATTT      960

TTGGACCGGC CAAGGACTAA CAAATGCGAA GGCAATTGCC AAGATCGTTT CCATTAATCA     1020

AGAACGACAG TCCGAGGTTC GAAGTCGATC AGATACCGAC TTAGTTCGGA CCGTAAACTA     1080

TGCCGACCCG AGATCAGTTT TGAGCTAATT AAACGCTCGA GGTTGCTCTC CCCTGGGAAA     1140

CCTTAAGTTT TTAGGTTACG GGGGAGTAT GGTTGCAAAG CTGAAACTTA AAGGAATTGA     1200

CGGAAGGGCA CCACCAGGGG TGGAGCCTGC GGCTTAATTT GACTCAACAC GGGAAAACTC     1260

ACCTGGTCCG GACATCGAAA GGATAGACAG ACTGATAGTC TTTCTTGATA CGTTGGTTGG     1320

TGGTGCATGG CCGTTCTTAG TTCGTGGAGT GATCTGTCAG GTTGATTCCG GTAACGGACG     1380

AAACCATATT CTCCATTTAA GGAATGCAAA AACTCAGTCA ATGTGTGTTG GCGCTAACAT     1440

GTGTTGACTG TAGCTGGTTG TCACTGAATA TCCGGGTGAA TTTGACAGTA TGAGTGAGAG     1500

TGTCAAAACT TGATCAAATA TTGTTGGAAA CAATTCGGGG ATGCTGTTCG CCTTTGCAAT     1560

AAACGGTGGA AGGCAACTGT TCACTGTCTT ATGGAGAGAC AAAGCA                     1606
```

(2) INFORMATION FOR SEQ ID NO:4:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:4:

GCATTGGTTT ACGCTGATGT AGCGA                                              25

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GAATCGCCGA AACAATCATC GAGCTA                                             26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GCCCTATTAA CTAGTTGGTA GTATAGAAGC                                         30

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GGCACACTAC TCCAACACTG AATTTG                                             26

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGCAGCGTTA AAACTGTCTC ACG                                                23

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ACCGCGGCTG CTGGCACCAG                            20

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AGCGAGTAAG GTGAATCTAG ATAAC                      25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CTTAAATTAC GTCCATTCCA AGCTG                      25

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CAATTTGCAA CAAGTAAGAG TTTTATC                    27

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CTGGTTGATT CTGCCAGT                              18

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
CGGTACTAGC GACGGGCGGT GTG                                              23

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CGTGAGACTG CGGACGGCTC AG                                               22

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CGGTGTGTAC AAAGGGCAGG GAC                                              23

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CCTCACAGTC TCTCCATGAC AC                                               22

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CTGCGGACGG CTCAGTAAAT CAGT                                             24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CCAGGACATC TTAGGGCATC ACAG                                             24
```

DNA-BASED DIAGNOSTIC TEST FOR DETECTING MYXOBOLUS, THE CAUSE OF SALMONID WHIRLING DISEASE

CROSS-REFERENCES TO RELATED APPLICATIONS

This is a continuation in part of provisional application U.S. Ser. No. 60/022,734, filed Jul. 26, 1996, which is incorporated herein by reference.

FEDERALLY SPONSORED RESEARCH AND DEVELOPMENT

This invention was made in part with Government support under Grant No. 14-48-0009-96-901, awarded by the U.S. Department of the Interior. The Government has certain rights in this invention.

FIELD OF THE INVENTION

The present invention is directed to compositions and methods for detecting the presence of the myxozoan parasite Myxobolus spp. in aquatic samples.

BACKGROUND OF THE INVENTION

Fish of the family Salmonidae are amongst the most commercially important of game fish. This taxonomic family includes such well known species as Atlantic salmon, brown trout, rainbow trout, coho salmon, and arctic char. Several species of salmonid fish are parasitized by the myxozoan parasite Myxobolus spp. (e.g., M. cerebralis, M. insidiosus, M. squamalis) which is responsible for the chronic inflammatory condition called whirling disease. The radical tail chasing behavior of infected fish, which characterizes the disease, results from pressure on the auditory capsule due to developmental stages of the parasite and the accompanying host's inflammatory response. The origins of the pathogen are suspected to be central Europe and Asia but movements of frozen and live trout have spread the agent to a total of 21 countries and 20 of the states in the USA. Recent increases in outbreaks of whirling disease have highlighted the vulnerability of stocks of salmonid fish in state and private hatcheries. The costs associated with control programs can be staggering. From 1965 to the present in California and Michigan alone these costs are estimated to exceed $30,000,000. This has brought to the forefront the concerns of transmission of pathogens between cultured and wild fish populations and the need to readily identify infected fish populations.

The phylum Myxozoa comprises a group of multicellular organisms that principally infect fish (Lom, J., *Parasitol. Today* 3:327 (1982)). Myxozoans found in freshwater have complex life cycles with alternating forms found in fish and aquatic oligochaete worms (Kent, M. L., et al., *Can. J. Zool.* 72:932 (1994); Wolf, K., et al., *Science* 255:1449 (1984); Wolf, K., et al., *J. of Fish Dis.* 9:83 (1986)). These stages are designated as myxosporean and actinosporean in their respective fish and worm hosts. The parasite stages designated as spores and triactinomyxons, respectively, emerge from the fish and worm hosts and they are infectious only for the other host (Wolf, K., et al., *Science* 255:1449 (1984)).

There are 6 Myxobolus spp. found in salmonid fish (Amandi, A., et al., *Fish Pathol.* 20:287 (1985); Hedrick, R. P., et al., *J. Aquat. Animal Health* 3:55 (1991); Hoffman, G. L., *J. Aquat. Animal Health* 2:30 (1990); Margolis, L., Aspects of Parasitology, E. Meerovitch, ed., McGill University, Montreal, pp. 135–226 (1982)). It is clear however, that the tropism for, and destruction of, cartilage by M. cerebralis causes it to be the most serious pathogen among this group. Because cartilage is a key structural component of the fish skeleton throughout life and particularly in young fish, it is understandable why the severity of whirling disease is inversely related to the age of the fish (Halliday, M. M., et al., *J. of Fish Biol.* 9:339 (1976); Markiw, M. E., *Aquaculture* 91:1 (1991)). It is among these very young trout that mortality has been attributed directly to the pathogen (Markiw, M. E., *Aquaculture* 91:1 (1991)). And, survivors, which act as carriers, may demonstrate lifelong deformities of the head, jaws, and spinal column because cartilage damage has interfered with subsequent bone deposition.

These pathogenic characteristics combined with the inability to eliminate the pathogen once established in natural waters, has made it the most serious fish pathogen facing the intermountain states of the US. Once believed to be strictly a disease among fish in aquaculture, whirling disease is now believed to be the major cause of the demise of wild rainbow trout populations in Montana, Colorado (Walker, P. G., et al., *An investigation to determine the disappearance of young wild rainbow trout in the upper Colorado River in Middle Park, Colo.*, Colorado Division of Wildlife, Montrose, Colo., 134 pp. (1995)), and Utah. *Myxobolus cerebralis* is now found in 20 states and appears to be spreading into and devastating wild populations of trout in the intermountain west.

Current methods for identification of M. spp. rely on the observation and measurement of spores as extracted from infected trout. This approach does not detect prespore stages which are present until spores develop 50–60 days post exposure to the infective stage. The problem is further exacerbated by the complex and changing alternate forms of the parasite found in the fish and aquatic oligochaete hosts. Additionally, immunodiagnostic methods have not shown the specificity required to distinguish spores of M. cerebralis from related Myxobolus spp. as found in rainbow trout.

Detection of the causative parasite is currently based on a definitive description of the spore consistent with its characteristic size and shape (Lom J, Hoffman G L (1970) *J Parasitol* 56: Proc 2nd Int Congr Parasit Abstr No 387) followed by confirmation of developmental stages or spores in cartilage of hematoxylin and eosin (H&E)—stained tissue sections (Thoesen, J C (1994) ed. *Suggested Procedures for the Detection and Identification of Certain Fish and Shellfish Pathogens*. 4th ed, Version 1, Fish Health Section, American Fisheries Society). The direct fluorescent antibody test has been used on occasion (Markiw M E (1989) *J Fish Dis* 12:137–141). A combination of digestion (Markiw M E, Wolf K (1974) *J Fish Res Bd Can* 31:15–20) and centrifugation (O'Grodnick J (1975) *J Wildl Dis* 11:54–57) techniques has been employed to detect the spores from cartilage in fish with Light infections. Although the later digestion/concentration procedure is effective in detecting the spore stage M. cerebralis, it is time consuming, labor intensive and destroys the prespore stages rendering them undetectable.

Accordingly, what is needed in the art is a means to rapidly detect the presence of M. spp. from an aquatic sample. In particular, what is needed is a means to detect this parasite with high specificity and sensitivity in both the fish and oligochaete hosts. The present invention provides these and other advantages.

SUMMARY OF THE INVENTION

In one aspect, the present invention is directed to an isolated nucleic acid of between 15 to about 2000 nucleotides in length which selectively hybridizes to an 18S rRNA gene of *Myxobolus cerebralis* as shown in SEQ ID NO:1. The invention also provides nucleic acids from other Myxobolus spp, such as *M. insidiosus* (SEQ ID NO:2) and *M. squamilis* (SEQ ID NO:3). The nucleic acids of the invention can be identified by their ability to be amplified by primers disclosed below. Generally, nucleic acids of the present invention are at least 18 nucleotides in length. The nucleic acid may be a deoxyribonucleic acid or a ribonucleic acid. Typically, the nucleic acids have at least 80% sequence identity to a single-stranded subsequence of SEQ ID NO:1.

In another aspect, the present invention is directed to a nucleic acid comprising a nucleic acid segment which selectively hybridizes to an 18S rRNA gene of *Myxobolus cerebralis* as shown in SEQ ID NO:1, wherein said nucleic acid segment selectively hybridizes to the same nucleic acid sequence as an oligonucleotide selected from the group consisting of:
5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:11), and
5'-CAATTTGCAACAAGTAAGAGTTTTATC-3 (SEQ ID NO:12).

In a further aspect, the present invention is directed to a method of detecting *Myxobolus cerebralis* nucleic acids in an aquatic sample. The method comprises the steps of contacting the aquatic sample with a nucleic acid comprising a nucleic acid segment capable of selectively hybridizing to SEQ ID NO:1 to form a hybridization complex; and detecting the hybridization complexes as an indication of the presence of *Myxobolus cerebralis* in the sample.

In one embodiment, the nucleic acid segment selectively hybridizes to the same nucleic acid sequence of an *Myxobolus cerebralis* 18S ribosomal nucleic acid as an oligonucleotide selected from the group consisting of:
5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3'(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:11), and
5'-CAATTTGCAACAAGTAAGAGTTTTATC-3 (SEQ ID NO:12).

In another embodiment, the method further comprises the step of amplifying the *Myxobolus cerebralis* nucleic acids in the sample. Conveniently, nucleic acids are amplified by the polymerase chain reaction. A nested amplification procedure may be employed in which the nucleic acids are amplified with primers which selectively hybridize to the same nucleic acid sequence as primers of SEQ ID NO:4 and SEQ ID NO:5 to form a first amplified segment. A subsequence of the first amplified segment is amplified with primers which selectively hybridize to the same nucleic acid sequence as primers of SEQ ID NO:6 and SEQ ID NO:7. In another embodiment, a single PCR amplification step is used to amplify *M. cerebralis* nucleic acids with primers consisting of SEQ ID NO:4 and 7.

In another embodiment, the *M. cerebralis* nucleic acid is contacted with the nucleic acid comprising a nucleic acid segment in situ. In yet another embodiment, *Myxobolus cerebralis* nucleic acid is a ribonucleic acid; in another, the aquatic sample is a tissue sample of a salmonid fish.

In a further aspect, the present invention relates to a diagnostic kit for use in determining the presence of *Myxobolus cerebralis* in an aquatic sample which comprises a container having a nucleic acid comprising a nucleic acid segment capable of selectively hybridizing to an 18S rRNA gene of *Myxobolus cerebralis* as shown in SEQ ID NO:1. In one embodiment, the nucleic acid comprising the nucleic acid segment selectively hybridizes to the same nucleic acid sequence of a *Myxobolus cerebralis* 18S ribosomal nucleic acid as an oligonucleotide selected from the group consisting of:
5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3'(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:1 1), and
5'-CAATTTGCAACAAGTAAGAGTTTTATC-3 (SEQ ID NO:12).

Alternative embodiments of the foregoing aspects of the present invention may be had by reference to the disclosure as a whole. The present invention provides utility in detection of *M. cerebralis* in, for example, salmonid fish or aquatic water columns.

DESCRIPTION OF THE PREFERRED EMBODIMENT

The present invention is directed to methods and compositions for detecting the presence of Myxobolus spp. nucleic acids in an aquatic sample. In preferred embodiments, the methods are used to detect *M. cerebralis* nucleic acids. The method comprises contacting an aquatic sample containing, or suspected of containing, *M. cerebralis* nucleic acids with a nucleic acid segment which is capable of selectively hybridizing to either one of the strands of the*M. cerebralis* 18S rRNA gene. The 18S rRNA gene codes for an RNA component of the small ribosomal subunit. Selective hybridization to the 18S rRNA gene (or its transcribed RNA) forms a hybridization complex. The presence of hybridization complexes indicates the presence of *M. cerebralis* in the sample. The method is useful for detecting the presence of *M. cerebralis* in an aquatic sample, such as parasitized salmonid fish or in the alternative host, oligochaete worms.

Definitions

Unless defined otherwise herein, all technical and scientific terms used herein have the same meaning as commonly understood by one of ordinary skill in the art to which this invention belongs. Singleton, et al., Dictionary of Microbiology and Molecular Biology, 2nd Ed., John Wiley and Sons, New York (1994), and Hale and Marham, The Harper Collins Dictionary of Biology, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

By "18S ribosomal nucleic acid" is meant the genomic deoxyribonucleic acid gene coding for the 18S rRNA of the small ribosomal subunit of eukaryotes, or its ribosomal ribonucleic acid (rRNA) transcription product. The term is inclusive of both mature and precursor forms of rRNA and their RNA complementary sequences.

By "aquatic sample" is meant a specimen, inclusive of the initial isolate and any subsequent portions thereof, in which the presence of 18S ribosomal ribonucleic or deoxyribonucleic acids from Myxobolus spp. is to be determined. Generally, the aquatic sample will be derived from a host or suspected host of *M. cerebralis* such as fish from the family Salmonidae, aquatic oligochaete worms, or from waters where any developmental stage of *M. cerebralis*, including multicellular developmental and sporogonic stages, occurs.

By "hybridization complex" is meant a duplex nucleic acid sequence formed by selective hybridization of two single-stranded nucleic acids with each other.

The term "identical" or "sequence identity" in the context of two nucleic acid sequences refers to the residues in the two sequences which are the same when aligned for maximum correspondence over a specified comparison window. Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natll. Acad. Sci. USA* 85:2444 (1988); by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp, *Gene* 73:237 (1988) and Higgins and Sharp, *CABIOS* 5:151 (1989); Corpet, et al., *Nucl. Acids Res.* 16:10881 (1988); Huang, et al., *Comp. Appl. in the Biosciences* 8:155 (1992), and Pearson, et al., *Methods in Molec. Biol.* 24:307 (1994). Alignment is also of ten performed by inspection and manual alignment.

By "isolated nucleic acid" is meant a substantially pure nucleic acid composition.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. A nucleic acid encodes another nucleic acid where it is the same as the specified nucleic acid, or complementary to the specified nucleic acid.

The terms "oligonucleotide" or "polynucleotide" probes are meant to include both double stranded and single stranded DNA or RNA. The terms also refer to synthetically or recombinantly derived sequences essentially free of non-nucleic acid contamination.

By "segment of nucleic acid" is meant a nucleic acid sequence of 10 to about 2000 nucleotides or nucleotide analogs in length or concatamers of such sequence.

By "selectively hybridizing" or "selective hybridization" is meant hybridization, under stringent hybridization conditions, of a nucleic acid sequence to a specified nucleic acid target sequence to a detectably greater degree than its hybridization to non-target nucleic acid sequences. Selectively hybridizing sequences have at least 80% sequence identity, preferably 90% sequence identity, and most preferably 100% sequence identity (i.e., complementary).

The term "subsequence" in the context of a referenced nucleic acid sequence refers to a contiguous sequence of fewer bases in length than the referenced nucleic acid.

Sample Collection and Treatment

Aquatic samples for use in this invention can be obtained by any number of methods well known to the skilled artisan including tow samples of aquatic waters, tissue samples from aquatic organisms, or gastric or intestinal contents of organisms taking nutrition from aquatic organisms. The samples may be subsequently processed, for example, to remove precipitated material, to concentrate or dilute the sample, filtered to exclude organisms of particular size, or cultured to enrich or deplete the population of particular organisms. Samples may also be fixed in solutions for subsequent histological analysis including in situ hybridization.

Typically, samples are permeabilized to allow egress of ribosomal nucleic acids or ingress of nucleic acid probes or primers of the invention. Liberation of nucleic acids from cells may be achieved by, for example, chemical/enzymatic methods such as lysing solutions, mechanical methods, or combinations thereof. Lysing solutions are typically composed of a buffered detergent solution (such as SDS) having a divalent metal chelator metal chelator (EDTA). Generally, these buffers are between pH 7.0 and 8.0. Mechanical methods, including French press, nitrogen cavitation, bead beater, or ultrasound sonification, may also be employed to permeabalize the cell. Alternatively, samples may be collected and dispersed in a lysing solution that also functions as a hybridization solution. Sambrook, et al., Molecular Cloning: A Laboratory Manual, Cold Spring Harbor, N.Y. (1989).

Nucleic Acids

Nucleic acids of the present invention are capable of selectively hybridizing to the 18S rRNA gene (or RNA equivalent) of M. spp. as disclosed here. In many embodiments the nucleic acids will be derived from *M. cerebralis*. Accordingly, nucleic acids of the present invention comprise a nucleic acid segment which selectively hybridizes to the same nucleic acid sequence as an oligonucleotide selected from the group consisting of:

5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3'(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:11), and

5'-CAATTTGCAACAAGTAAGAGTTTTATC-3 (SEQ ID NO:12).

Generally, nucleic acid segments of the present invention are at least 15, 16, 17, or 18 nucleotides in length; preferably, at least 19, 20, or 21 nucleotides in length; and most preferably at least 22, 23, 24, 25, 26, 27, 28, 29 or 30 nucleotides in length. Nucleic acids are typically from less than about 2000 base pairs, more typically less than about 1000, and generally less than about 500. Conveniently, nucleic acids are 100 base pairs or less.

Nucleic acids comprising a nucleic acid segment capable of selectively hybridizing to the 18S rRNA gene of *M. cerebralis* and other species may be employed as probes for detection of 18S ribonucleic acids, or as primers for their amplification. It will be understood by those of skill in the art that the sensitivity of the hybridization assays may be enhanced through the use of a nucleic acid amplification system which increases the amount of M. spp. 18S ribosomal nucleic acid being detected. Amplification may be achieved at any time prior to detection including before or after formation of the hybridization complexes.

Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., eds., American Society for Microbiology, Washington, D.C. When such amplification methods are used to enhance the sensitivity of the hybridization assay, the amplified nucleic acid is subsequently detected in the hybridization assay.

As those of skill will appreciate, the amplification schemes which can be used also extend to modifications of the basic amplification methods. For example, in PCR nested-amplification a first round of amplification is performed with a single primer pair (e.g., SEQ ID NOS: 4 and 5, or 8 and 9). The amplification product is subject to a second round of amplification using a second primer pair that is specific for a sequence internal to that amplified by the first primer pair (e.g., SEQ ID NOS: 6 and 7, or 10 and 11). In this approach, high sensitivity is achieved and reamplification serves to verify the specificity of the first-round amplification. In addition, transfer of reaction products from the first reaction serves to dilute out inhibitors that might be present in the sample. In addition, single round PCR amplifications can be used. In these embodiments, preferred primers are those that hybridize to the same sequence as SEQ ID NO:4 or SEQ ID NO:7.

The nucleic acids of the present invention may be a composition of RNA or DNA or chimera thereof. In addition, analogs of nucleosides may be substituted for naturally occurring nucleosides. The advantage of analogs would include greater stability, resistance to nuclease activity and ease of signal attachment. The nucleic acids of the present invention may be chemically synthesized using commercially available methods and equipment. Methods of synthesizing nucleic acids are well known in the art. Deoxynucleotides may be synthesized chemically according to the solid phase phosphoramidite triester method described by Beaucage & Caruthers, *Tetrahedron Lett.* 22:1859 (1981), e.g., using an automated synthesizer, e.g., as described in Needham-VanDevanter et al., *Nucl. Acids Res.* 12:6159 (1984).

To obtain large quantities of oligonucleotides, one can also clone the desired sequence using traditional cloning methods, such as described in Sambrook, et al., Molecular Cloning: A Laboratory Manual, Cold Spring Harbor, N.Y. (1989), or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host. The DNA probes can be purified from the host cell by lysis and nucleic acid extraction, treatment with selected restriction enzymes, and further isolation by gel electrophoresis. The use of polymerase chain reaction technology can also be used to obtain large quantities of probe. (See U.S. Pat. No. 4,683,202).

Hybridization Format and Conditions

As those of skill in the art will understand, selective hybridization of a single-stranded nucleic acid of the present invention to a single-stranded 18S ribosomal nucleic acid such as the 18S rRNA gene or an RNA equivalent (e.g., ribosomal RNA) results in formation of hybridization complex comprising a nucleic acid duplex structure. Detection of the hybridization complex is an indication of the presence of M. spp. in the aquatic sample.

The aquatic sample, or a portion thereof, may be assayed by hybridization formats well known to the skilled artisan, including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support.

In some preferred embodiments, in situ hybridization is used. In in situ hybridization, the target nucleic acid is liberated from its cellular surroundings such as to be available for hybridization within the cell while preserving the cellular morphology for subsequent interpretation and analysis. The following articles provide an overview of the various hybridization assay formats: Singer et al., *Biotechniques* 4:230 (1986); Haase et al., Methods in Virology, Vol. VII, pp. 189–226 (1984); Wilkinson, In situ Hybridization, D. G. Wilkinson ed., IRL Press, Oxford University Press, Oxford; and Nucleic Acid Hybridization: A Practical Approach, Hames, B. D. and Higgins, S. J., eds., IRL Press (1987).

Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

Stringent hybridization conditions in the context of nucleic acid hybridization assay formats, such as those described above, are sequence dependent, and are different under different environmental parameters. An extensive guide to the hybridization of nucleic acids is found in Tijssen, Laboratory Techniques in Biochemistry and Molecular Biology—Hybridization with Nucleic Acid Probes, Elsevier, N.Y.

(1993). Generally, highly stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular nucleic acid of the present invention. This occurs, e.g., when a copy of a nucleic acid is created using the maximum codon degeneracy permitted by the genetic code. Stringent hybridization conditions refer to conditions under which a probe will hybridize substantially to its target subsequence, but to no other sequences. Stringent conditions are sequence-dependent and will be different in different circumstances. Longer sequences hybridize specifically at higher temperatures.

The degree of complementarity (sequence identity) required for detectable binding will vary in accordance with the stringency of the hybridization medium and/or wash medium. The degree of complementarity will optimally be 100 percent; however, it should be understood that minor variations in the rRNA may be compensated for by reducing the stringency of the hybridization and/or wash medium as described below. Thus, despite the lack of 100 percent complementarity under reduced conditions of stringency, functional nucleic acids of the present invention having minor base differences from their M. spp. 18S nucleic acid targets are possible. Therefore, under hybridization conditions of reduced stringency, it may be possible to construct an oligonucleotide having substantial identity to an oligonucleotide complementary to the target sequence while maintaining an acceptable degree of specificity. Substantial identity in the context of nucleic acids means that the two molecules hybridize to each other under stringent conditions. Generally, stringent conditions are selected to be about 5° C. to 20° C. lower than the thermal melting point ($T_m$) for the specific sequence at a defined ionic strength and pH. The hybridization format or buffers are not critical aspects of the present invention and those of skill will recognize that further advances, improvements, or modifications in nucleic acid hybridization, amplification, and detection are within the scope of the invention.

Detection of Hybridization Complexes

Detection of hybridization complexes is not a critical aspect of the present invention and can be accomplished by any number of methods currently known or later developed. Nucleic acids capable of selectively hybridizing to the 18S rRNA gene or rRNA of *M. cerebralis* can be labeled by any one of several methods typically used to detect the presence of hybridized nucleic acids. One common method of detection is the use of autoradiography or autofluorography using probes labeled with $^3H$, $^{125}I$, $^{35}S$, $^{14}C$, or $^{32}P$, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I, by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}P$ phosphate or $^{14}C$ organic acids, or esterified to provide a linking group to the label. Base analogs having nucleophilic linking groups, such as primary amino groups, can also be linked to a label.

Non-radioactive probes are of ten labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g. luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., *Nucl. Acids Res.* 12:3435 (1984)) and synthetic oligonucleotides have been coupled directly with alkaline phosphatase (Jablonski, E., et al., *Nucl. Acids. Res.* 14:6115 (1986); and Li P., et al., *Nucl. Acids Res.* 15:5275 (1987)).

Kits

The nucleic acids of this invention can be included in a kit which can be used to rapidly determine the presence of M. spp. in an aquatic sample. The kit includes all components necessary to assay for the presence of the Myxobolus spp. (e.g., *M. cerebralis*) 18S ribosomal nucleic acid in a sample. The kit typically includes a stable preparation of nucleic acids comprising a nucleic acid segment capable of selectively hyridizing to the 18S rRNA gene of *M. cerebralis*. Further, the kit may also include hybridization solution in either dry or liquid form for the hybridization of *M. cerebralis* 18S nucleic acids of the present invention, as well as a solution for washing and removing undesirable and non-hybridized nucleic acids, a substrate for detecting the hybridization complex, and instructions either printed or electronically stored.

Although the present invention has been described in some detail by way of illustration and example for purposes of clarity of understanding, it will be obvious that certain changes and modifications may be practiced within the scope of the appended claims.

EXAMPLE 1

Example 1 describes the isolation and sequencing of the 18S rRNA gene of *Myxobolus cerebralis*.

Both myxosporean and actinosporean spores were generated in the laboratory at the Fish Health Research Center, National Biological Survey, Leetown, W. Va. The alternating stages represented a single source of spores used to initiate the infections in oligochaetes and then fish. *Myxobolus cerebralis* spores were obtained directly from infected rainbow trout (*Oncorhynchus mykiss*) tissues using the pepsin trypsin digest as described by Markiw and Wolf (*J. of the Fisheries Res. Board of Canada* 31:15 (1974)). Partially purified spores were stored at −20° C. until used. Actinosporean stages were obtained as described by Markiw (*J. of Fish Dis.* 12:137 (1989)) following experimental infections of the oligochaete (*Tubifex tubifex*). The actinosporean stages were partially purified using PERCOLL (modified-sucrose) gradient centrifugation. These stages were also stored at −20° C. prior to use.

A. DNA Extractions

Actinosporeans (6×10$^6$) were resuspended in 500 µL of lysis buffer (100 mM NaCl, 10 mM Tris pH 7.6, 10 mM EDTA, 0.2% SDS, 0.2 mg/ml proteinase K) and incubated at 37° C. for 16 hours. Phenol and chloroform were then added to the digested sample and mixed on a rocker platform for 10 min. The upper phase was removed following centrifugation for 10 min at 8,000 rpm in a microcentrifuge. This extraction was repeated a second time followed by a single treatment with isoamyl alcohol/chloroform. Sodium acetate (3 M pH 6.9) was added with 2 volumes of 100% cold ethanol to precipitate the DNA. DNA was collected by centrifugation for 10 min at 14,000 rpm in a microcentrifuge. The pellet was washed once in 70% ethanol and air-dried for 15 min prior to resuspension in TE buffer (10 mM Tris pH 8.0, 1 mM EDTA). DNA content was determined by spectrophotometry.

Optimal recovery of genomic DNA was obtained from Myxosporean stages of *M. cerebralis* spores (2×10$^6$) following heating in a microwave oven. The spores were pelleted briefly in a microfuge tube and air dried for 15 minutes. The dried pellet was placed in an 800 watt microwave oven and heated for 1 minute. The spores were then resuspended in 500 µL of lysis buffer and treated as previously described for actinosporeans.

B. Oligonucleotide synthesis

Primers for DNA sequencing and PCR were synthesized on a ABI DNA synthesizer, model #394. Oligonucleotides were then desalted on a NAP™ 5 desalting column (Pharmacia Biotech, Inc., Alameda, Calif.) and diluted in water to working concentrations for PCR and DNA sequencing, 20 pmoles/µL and 10 ng/µL, respectively.

Primer Sequences:

| | | |
|---|---|---|
| 18e | 5'-CTGGTTGATTCTGCCAGT-3' | (SEQ ID NO:13) |
| 18g' | 5'-CGGTACTAGCGACGGGCGGTGTG-3' | (SEQ ID NO:14) |
| Tr5-3 | 5'-CGTGAGACTGCGGACGGCTCAG-3' | (SEQ ID NO:15) |
| Tr3-1 | 5'-CGGTGTGTACAAAGGGCAGGGAC-3' | (SEQ ID NO:16) |
| Tr5-6 | 5'-GGCAGCGTTAAAACTGTCTCACG-3' | (SEQ ID NO:8) |
| Tr3-6 | 5'-CCTCACAGTCTCTCCATGACAC-3' | (SEQ ID NO:17) |

C. PCR Amplification of 18S ribosomal nucleic acids

The actinosporean 18S rRNA gene was amplified using primers 18e and 18g'. The myxosporean 18S rRNA gene was amplified using a nested PCR developed using known sequences obtained from the actinosporean. In the first round, primer Tr 5-3 and primer Tr 3-1 were used. In the second, round primer Tr 5-6 and primer Tr 3-6 were used. The 18S ribosomal nucleic acid fragments were amplified in standard 50 µL reactions containing 10 mM Tris-HCl pH 8.3 (at 25° C.), 50 mM KCl, 1.5 mM MgCl$_2$, 0.001 % w/v gelatin, 400 µM dNTP's, 5 µM trimethyl ammonium chloride, 40 pmoles of each primer, and 2 U Taq polymerase. The PCR thermal cycler used was a model PTC-100 (MJ Research, Watertown, Mass.). Forty cycles of 1 min at 95° C., followed by 2 min at 45° C., followed by 4.5 min at 72° C. were used in the amplification. The amplification cycles were preceded by a denaturation step where samples were held at 95° C. for 5 min. The thermal cycler program finished with an extended elongation step where samples were held at 72° C. for 10 min.

D. Cloning of PCR Products

The actinosporean 18S ribosomal nucleic acids were cloned into pCR II using the TA cloning kit (Invitrogen, San Diego, Calif.). The myxosporean 18S rRNA gene was cloned into pNoTA using the PRIME PCR CLONER™ Kit (5 Prime→3 Prime, Boulder, Colo.).

E. Sequencing of 18S ribosomal nucleic acids

The 18S rRNA gene sequence was derived by oligonucleotide directed dideoxynucleotide chain termination sequencing using the TAQuence sequencing kit (United States Biochemical Corporation, Cleveland, Ohio). Sequencing reactions were run on 0.4 mm thick 6% polyacrylamide gels in a SEQUI-GEN II SEQUENCING® System (BioRad, Hercules, Calif.). Mac DNASIS™ v 3.5 (Hitachi Software Engineering America, Ltd., San Bruno, Calif.) was used to align sequences. The original primers used, 18e and 18g', were successful in amplifying the 18S rRNA gene from the actinosporean. This gene was 1934 bp in length (SEQ ID NO:1).

EXAMPLE 2

Example 2 describes specifically detecting *M. cerebralis* in a tissue sample from salmonid fish.

Cartilage samples from the head of a salmonid fish were homogenized and incubated for 4 hours at 55° C. in 500 µL of lysis buffer as described above. The lysate was extracted twice with equal volumes of phenol/chloroform. The clarified lysate was extracted with isoamyl alcohol/chloroform. The supernatant containing DNA was treated with ethanol. The precipitated DNA was washed and dried and resuspended in TE buffer and content quantified by spectrophotometry. Samples were diluted to 50 ng/mL for PCR amplification.

In the first round of PCR, 40 picomoles of primer Tr5-16 5'-GCATTGGTTTACGCTGATGTAGCGA-3' (SEQ ID NO:4) and 40 picomoles of primer Tr3-16 5'-GAATCGCCGAAACAATCATCGAGCTA-3'(SEQ ID NO:5) were used to amplify a specific fragment of *Myxobolus cerebralis* rRNA gene of 1296 base pairs. This reaction used a 150 ng of template DNA from the sample. The reaction contained 1.5 mM MgCl$_2$, 10 mM Tris-HCl pH 8.3 (at 25° C.), 50 mM KCl, 0.1% w/v gelatin, 5 µM trimethyl ammonium chloride and 2 units of Taq polymerase.

In round 2 of the amplification, 1 µL of round 1 product was transferred to a second PCR containing the above reactants with two other primers Tr5-17 5'-GCCCTATTAACTAGTTGGTAGTATAGAAGC-3'(SEQ ID NO:6) and Tr3-17 5'-GGCACACTACTCCAACACTGAATTTG-3'(SEQ ID NO:7) that yielded a 415 base pair product.

The thermal cycler conditions used in both rounds were:

| Step No. | Temp. (°C.) | Time (min.) |
|---|---|---|
| 1 | 94 | 5 |
| 2 | 94 | 1 |
| 3 | 65 | 2.5 |
| 4 | 72 | 1.5 |
| 5 | Return to Step 2 - 34 times | |
| 6 | 72 | 7 |
| 7 | 16 | hold |

As an alternative, the following primers are used under the same conditions as described with the exception that the annealing temperature was 45° C. during the thermal cycling:

Round I

Tr5-6  5'-GGCAGCGTTAAAACTGTCTCACG-3'  (SEQ ID NO:8)

Tr3-7  5'-ACCGCGGCTGCTGGCACCAG-3'    (SEQ ID NO:9)

Round II

Tr5-                                  (SEQ ID NO:10)
13 5'-AGCGAGTAAGGTGAATCTAGATAAC-3', and Tr3-                                  (SEQ ID NO:11)
13 5'-CTTAAATTACGTCCATTCCAAGCTG-3'

To detect the product, a 1.5% agarose gel containing TAE buffer is poured to 7 mm thickness. A total of 15 µL of round 2 product is mixed with 4 µl of 30% glycerol and then run on the gel for 1.5 hours at 1.5 V/cm. A positive control sample containing the plasmid p18MyG2-3 containing a single copy of the 18 rRNA gene of *M. cerebralis* and a negative control are included in each test. The band corresponding to the round 2 product is visualized on a UV transilluminator after ethidium bromide staining of the gel.

A semi-quantitative determination of the level of *M. cerebralis* in an aquatic sample is provided by nested amplification using nucleic acids comprising nucleic acid segments which selectively hybridize to the same nucleic acid sequence of *M. cerebralis* 18S ribosomal nucleic acid as primers of SEQ ID NO:4 and 5 for round 1 amplification, and primers of SEQ ID NO:6 and 7 for round 2 amplification. With high levels of *M. cerebralis* 18S ribosomal nucleic acid in the initial isolate (e.g., at high levels of infection of salmonid fish or of a water column) two fragments of 417 and 510 bases in length are readily detected by, for example, agarose gel electrophoresis/ethidium bromide staining. At low levels of infection, however, relative amounts of the 510 base fragment is greatly reduced and is typically undetectable by agarose gel electrophoresis. Thus, use of this semi-quantitative method can be used to readily assess levels of infection. Of course, quantitative determination of *M. cerebralis* in a sample using nucleic acids of the present invention can be assessed by any number of methods known to those of skill in the art (e.g., construction of standard curves using known amounts of *M. cerebralis* 18S ribosomal nucleic acid). For a review of quantitative PCR see, e.g., Ferre, *PCR Methods Applic.* 2:1.

EXAMPLE 3

The following example demonstrates non-nested PCR amplification of *M. cerebralis* 18S ribosome DNA.

PCR amplification was carried out as described in Example 2 except that the following primers are used:

TR5-16 5'-GCATTGGTTTACGCTGATGTAGCGA-3' (SEQ ID NO:4)

TR3-17 5'-GGCACACTACTCCAACACTGAATTTG-3- (SEQ ID NO:7)

The thermal cycler conditions were as follows:

| Step No. | Temp. (°C.) | Time (min.) |
|---|---|---|
| 1 | 95 | 5 |
| 2 | 94 | 1 |
| 3 | 65 | 0.5 |
| 4 | 72 | 0.5 |
| 5 | Return to Step 2 - 34 times | |
| 6 | 72 | 10 |
| 7 | 16 | hold |

Reagents concentrations were as follows: primers—40 pmoles each/reaction, MgCl—1.5 mM final concentration, Taq polymerase 2 U/reaction, TMAC—5 $\mu$M final concentration, dNTP's 400 $\mu$M.

EXAMPLE 4

The following provides PCR amplification of the 18s rRNA gene or the corresponding RNA from most Myxobolus species. These primers and conditions are useful for amplifying a fragment of between about 1500 and 2000 nucleotides in length, usually about 1700.

PCR amplification was carried out as described above except that the following primers are used:

```
                                        (SEQ ID NO:18)
MX5 5'-CTGCGGACGGCTCAGTAAATCAGT-3' and (SEQ ID NO:19)
MX3 5'-CCAGGACATCTTAGGGCATCACAG-3'.
```

The thermal cycler conditions were as follows:

| Step No. | Temp. (°C.) | Time (min.) |
|---|---|---|
| 1 | 94 | 5 |
| 2 | 94 | 1 |
| 3 | 65 | 2.5 |
| 4 | 72 | 1.5 |
| 5 | Return to Step 2 - 35 times | |
| 6 | 72 | 7 |
| 7 | 16 | hold |

EXAMPLE 5

The following example demonstrates an in situ hybridization assay for *M. cerebralis* 18S ribosome DNA.

MATERIALS AND METHODS

Experimental exposures

Fish were experimentally exposed to the infectious stage of the parasite (triactinomyxon spore) derived from its alternate oligochaete host previously exposed to the myxosporean spore. The preparation and production of the infective stages for both hosts are described below.

Spore preparation

Adult rainbow trout from an epizootic at Mt. Whitney, California Department of Fish and Game, Rancho Cordova, Calif. were transported to the laboratory and maintained in 130 L aquaria at 15° C. until used for spore preparation. The spores were prepared from these fish on the day of the experimental exposures by collecting the heads and then grinding them in a blender with two volumes of distilled water until most of the bone and cartilage were crushed. The resulting slurry was filtered through two layers of gauze to remove large pieces of bone and tissue, concentrated with a plankton centrifuge, the pellet resuspended in distilled water and the spores enumerated by counting with a hemocytometer.

Experimental exposure of oligochaetes and triactinomyxon (TAM) production

Tubificid oligochaetes were collected from the settling basins of the incoming water to the Mt. Whitney Hatchery. Oligochaetes were separated and divided into two equal groups and then placed into 10 L container aquaria with 2.5 cm sterilized sand substrate covered with 20.0 cm of dechlorinated tap water. The oligochaetes (mixed species population) were maintained at 15° C. with artificial light on a 16 h day 8 h night cycle. Approximately ⅓ of the water was changed every three days. Prior to addition of the spore suspension, the water was drained to reach a level of 1 cm above the substrate.

A freshly prepared spore suspension from five heavily infected rainbow trout heads was added to one of the aquaria. This inoculum contained $10^7$ spores per 20 g of worms. After 4 h of incubation with spores, water was added to bring the level to 1 cm. The control aquaria was treated similarly but no spores were added. An airstone and pump provided mechanical aeration to the oligochaete containers. Production of TAMs was detectable in the treated aquaria following filtration of the water through a 25 µm nytex screen at 90 d after the oligochaetes were exposed to mature spores.

Samples were collected at 24 h, 4, 8, 14, 21 and 28 d, and at 5, 6, 10, 11, 12, 13 and 14 wk post exposure. Approximately 50 oligochaetes were separated from the substrate with forceps at each sampling, euthanized with 500 ppm benzocaine and then placed in 10% neutral buffered formalin.

For negative controls, oligochaetes were treated in the same manner as the exposed animals but without the parasite and were collected and fixed at the same time as the exposed groups.

Experimental exposure of fish to TAMs

Rainbow trout alevins (mean wt=1.0 g) from a commercial farm were hatched from eggs in the laboratory and maintained at 15° C. well water until exposed to TAMs.

Triactinomyxons released into the water by worms at 90 d post exposure to mature spores were collected by siphoning the water into a bucket and then poured through a 20 µm nytex screen. The concentrated parasites were retained on the screen, suspended in a 50 ml distilled water for counting and held at 4° C. until added to the water containing the fish to be infected.

After a thorough gentle mixing of the TAM suspension, a 100 µl sample was removed with a micropipetter and then transferred to a 60 mm petri dish with a 2 mm grid (Fisher Scientific, Pittsburgh, Pa.). A 20×40 mm coverglass (Fisher Scientific, Pittsburgh, Pa.) was placed on the sample to stabilize the suspension and all parasites on the dish were counted. The number of parasites counted was multiplied by ten and by the total volume of the TAM suspension to obtain an approximate total number of parasites. In an attempt to optimize the accuracy of determining numbers of infective forms, only TAMs with tightly packed sporoplasms at the apical end were included for infectivity studies. Exposure dosage was calculated as number of TAMs/fish.

Approximately 100 fish were exposed to 2,000 TAMs/fish for 2 h in 15° C. Following exposure, the fish were transferred to a 130 L tank supplied with flow-through well water maintained at 15° C. A control group of alevin trout hatched from the same egg lot were maintained under same conditions but not exposed to TAMs. Fish were collected from the experiment and control groups at 2, 12 and 24 h and at 4 mo post treatment.

Tissue fixation and histological preparation

Immediately after collection, fish and oligochaetes were sacrificed by an overdose of 500 ppm benzocaine solution, fixed in neutral buffered formalin for 24–48 h and then changed to 70% ethanol. Using standard procedures (Humason, GL (1979) Animal tissue techniques. Freeman, San Francisco), fish and worms were embedded in paraffin, sectioned to 5–6 µm, adhered onto positively charged slides (Fisher Scientific, Pittsburgh, Pa.) and then stored in slide boxes with desiccant at room temperature until used for ISH and H&E staining. Tissues designed for long-term storage or retrospective studies were stored as paraffin blocks at room temperature.

Primers

A cocktail of three primers specific for myxozoan sequences (Tr) including Tr 5-16, Tr 3-16 and Tr 3-17 directed at target sequences of *M. cerebralis* served as probes. The primers were synthesized by Gibco BRL Life Technologies (Grand Island, N.Y.) and their sequences are given below in the 5-3' direction.

```
Tr 5-15 GCATTGGTTTACGCTGATGTAGCGA  (SEQ ID NO:4)

Tr 3-16 GAATCGCCGAAACAATCATCGAGCTA (SEQ ID NO:5)

Tr 3-17 GGCACACTACTCCAACACTGAATTTG (SEQ ID NO:7)
```

Probe labeling

An equivolume mixture of the three primers was labeled by tailing the 3'-end with digoxigenin-labeled deoxyuridine triphosphate (DIG-dUTP) using the GENIUS™ 6 tailing kit (Boehringer Manheim, Indianapolis, Ind.). The labeling procedure was followed according to the manufacturer's instructions. Briefly, the reagents from the kit were added to a sterile microfuge tube on ice in the following order: 5×reaction buffer, cobalt chloride solution, DIG-dUTP, 200 pmole primer cocktail (equivolume mixture), dATP solution and terminal transferase. The reaction mixture was gently mixed with a pipet, incubated in a 37° C. waterbath for 15 min, immediately placed on ice and then concentrated in a spin vacuum for 45 min with open lids. A blue precipitate indicated the presence of the labeled product. The labeled probe was resuspended in 20 μl Dnase-free water and stored at −20° C. if not used immediately.

Techniques for ISH

The ISH protocol used in our trials was based on Gan et al. (1994) *J Histotech* 17:313–319. Several steps were modified and optimized as appropriate for the probe and tissue samples we used. To prevent DNA contamination, all steps prior to and during the hybridization step were kept clean and sterile if possible. Gloves were used to handle tissue sections in all stages of the procedure. Buffers and materials used before and during the hybridization step were sterilized in an autoclave.

Tissue deparaffinization

Tissue sections were deparaffinized with three changes of xylene for 10 min each, hydrated with ethanol (100, 95, 80, 70 and 50%) for 3 min each and then rinsed in sterile distilled water. Tissue sections were finally equilibrated in Tris buffer (0.2 M Tris HCl+2.0 mM CaCl, pH 7.2) prior to proteinase K treatment.

Permeabilization of tissues

For optimum probe penetration to target tissues, sections on slides were permeabilized with 50 μg/ml proteinase K (Gibco BRL Life Technologies, Grand Island, N.Y.) in Tris buffer for 30 min at 37° C. After incubation with the enzyme solution, the tissues were rinsed twice with PBS for 10 min each. Following final rinses with sterile distilled water, the tissues were equilibrated in 2×SSC (0.3 M NaCl+0.03 M sodium citrate, pH 7,2) for 5–10 min prior to prehybridization.

Prehybridization

Prehybridization for 2 h was carried out to reduce background in tissue sections. The following reagents used for preparation of the prehybridization and hybridization solutions were molecular biology grade and were purchased from Sigma (St. Louis, Mo.). The reagents contained in the prehybridization solution are as follows (per 1.0 ml solution): 0.51 mil deionized formamide, 0.20 ml 20×standard saline citrate (1×SSC=0.15 M NaCl, 0.015 M sodium citrate, pH 7.0), 0.05 ml 10 mg/ml heat-denatured sperm DNA, 0.20 ml 50% (v/v) dextran sulfate and 0.02 ml 50×Denhardt's solution. To minimize nonspecific hybridization of the tailed probe to related homologous sequences in the target DNA, Poly A (included in the Genius 6 kit) was added to the prehybridization mixture at 0.1 mg/ml. Prehybridization solution (0.5 ml) was added to each slide and then incubated without coverslips at room temperature in a humid chamber.

Hybridization

Following prehybridization, the solution was discarded, the slides rinsed in 2×SSC and briefly dried prior to the addition of the hybridization solution (same components as the prehybridization mixture). The probe was diluted at 1:1000 (10 fmole/$\mu$l) with the hybridization solution. Both the tissue and the hybridization solution were simultaneously denatured at 100° C. for 10 min using a heater block (Lab-line Instruments, Melrose Park, Ill.). The tissues were covered with Dnase-free coverslips (RPI, Mount Prospect, Ill.) and then incubated overnight at 40° C. in a humid chamber.

Stringency washes

Unbound probe was removed by washing the tissues with two changes of 2×SSC for 30 and 15 min each in a shaking incubator at 40° C. Following two rinses in 1×SSC for 10 min, the sections were rinsed in 0.5×SSC for 10 min at 37° C. The tissues were equilibrated in buffer 1 (100 mM TrisHCl, 10 mM NaCl, pH 7.5) for 10 min and then blocked with buffer 1 containing 2.0% sheep serum and 0.3% TRITON® X-100 nonionic detergent (Fisher Scientific, Pittsburgh, Pa.) for 30 min.

Detection of hybridization signals

Alkaline phosphatase (AP)-labeled sheep anti-DIG antibody conjugate (Boehringer Manheim, Indianapolis, Ind.) was diluted 1:1000 in buffer 1 containing 1.0% sheep serum and 0.3% Triton X-100. The conjugate solution (0.5–1.0 ml) was carefully added to a dry section and incubated without a coverslip at 4° C. overnight in a humid chamber. Following equilibration to room temperature for 30 min, the slides were rinsed twice with buffer 1 for 10 min each with mild shaking followed by a final rinse with buffer 2 (100 mM Tris-HCl, 100 mM NaCl, 50 mM MgCl2, pH 9.5 for 10 min.

The substrate (Boehringer Manheim, Indianapolis, Ind.) was prepared during equilibration by adding 45 $\mu$l nitroblue tetrazolium (NBT) and 35 $\mu$l of 5-bromo-4-chloro-3indoyl phosphate (BCIP) to 10 ml of buffer 2. The tissue sections were incubated with the substrate solution for 4–8 h at room temperature in a humid chamber. The intensity of the signal was examined microscopically before the reaction was stopped by three changes with distilled water of 3 min each. To enhance the tissue morphology against the signal, sections were counterstained with 0.5% aqueous Bismarck Brown Y (Sigma, St. Louis, Mo.) for 3 min. The slides were then rinsed with distilled water followed by a brief dehydration in 70 and 100% EtOH, air dried and finally mounted with a coverslip using a permanent mounting medium (Permount, Harleco, N.J.). Hybridization signals were evaluated by light microscopy for areas showing a purple precipitate where the probe had bound to M. cerebralis DNA.

Optimization of ISH protocol

To optimize the protocol, the following parameters were modified: a) concentration and length of solubilization with proteinase K, b) dilution of probe and anti-DIG-AP antibody conjugate, c) temperature and length of incubation of anti-DIG antibody, d) temperature and duration of stringency washes and e) temperature and length of incubation of BCIP/NBT substrate.

Specificity of hybridization signals

To demonstrate the specificity of the signals, uninfected tissue sections and infected tissues showing the developmental stages of M. cerebralis (as confirmed in H&E-stained sections) were hybridized with an excess of the labeled and unlabeled probe. Rainbow trout infected with C. shasta or the PKX organism or the sculpin infected with a Myxobolus sp. in the cartilage were also examined to further evaluate probe specificity.

RESULTS

Optimization of the Protocol

Solubilization of the tissues with 50 $\mu$g/ml proteinase K resulted in strong hybridization signals compared to untreated tissues or those treated with lower enzyme concentrations (1, 5, 10 and 25 $\mu$g/ml). On the other hand, enzyme concentrations greater than 50 $\mu$g/ml destroyed the tissue morphology.

The optimum dilution of the probe was 1:1000 (10 fmole/$\mu$l). Increasing the concentration of the probe to 20 fmole/$\mu$l did not significantly increase the intensity of the hybridization signal but did increase backgrounds. Significantly weak signals were observed at 5 fmole/$\mu$l probe concentration. A simultaneous denaturation of the tissue and the hybridization solution at 100° C. for 10 min resulted in significantly strong signals. Signals were greatly reduced when the tissue and the hybridization solution were separately denatured as suggested in other ISH protocols.

Post hybridization washes at 40° C. resulted in decreased backgrounds compared to parallel washes conducted at room temperature. In contrast, post hybridization washes at 70° C. eliminated even specific binding of the probe.

The optimum dilution of the anti-DIG-AP antibody was 1:1000 at an incubation temperature of 4° C. for 12 h or overnight. Attempts to shorten the anti-DIG antibody reaction by incubating at higher temperatures (10 and 15° C.) gave variable signals.

Binding with the NBT-BCIP substrate at room temperature for 6 h gave a strong signal and minimal backgrounds. Incubating the substrate beyond 8 h did not significantly increase the signal but did increased nonspecific staining.

Detection of parasite DNA

Hybridization signals were observed as purple precipitates in target tissues indicating the binding of the labeled probe to M. cerebralis DNA. Binding of labeled probe was eliminated when tissues infected with the parasite were treated first with an excess of the unlabeled probe. Alternatively, signals were not observed in fish or oligochaete tissues unexposed to the parasite when hybridized with an excess of the labeled probe. Furthermore, the probe did not bind to rainbow trout tissues infected with the other myxosporean parasites tested including *C. shasta*, the PKX organism, or the sculpin infected with a *Myxobolus* sp.

Location of Bound Probes in Infected Trouts and Oligochaetes

Hybridization of the labeled probe to target DNA in different locations depended on the time post exposure to the parasite. Fish examined at 2 h post exposure demonstrated positive binding to cells in the epithelium of the fins, skin and gills. These cells were aggregates or single sporoplasms and were more easily detected by ISH than in parallel sections stained with H&E. Trophozoite and sporogonic stages of the parasite were observed in numerous tissues including peripheral nerves, the cranial cartilages and vertebral column of fish examined at 20 d up to 4 mo post exposure. In oligochaetes, signals were detected in the mucosal epithelium of the intestines from 28 d up to 14 wk after exposure to mature spores of *M. cerebralis*. Parasite stages observed ranged from single to multicellular trophozoites to pansporoblasts and to nearly mature spores. Hybridization signals were not observed in fish or oligochaetes not exposed to the parasite. Some non-specific binding of the probe to unknown cellular or enzymatic components was observed in the intestines of fish and oligochaetes.

DISCUSSION

The ISH protocol specifically detected all known stages of *M. cerebralis* in its fish and oligochaete hosts. This procedure provides an extremely useful tool for the nonradioactive detection of the parasite in paraffin-embedded fixed tissues. Although additional myxosporeans need to be tested, there was no evidence that the probe bound to the PKX organism, *C. shasta*, or a cartilage dwelling *Myxobolus* sp.

In these experiments, fish and worm tissues were initially fixed in 10% neutral buffered formalin based on previous findings indicating the usefulness of the fixative for DNA analysis (see, e.g., Goelz et al. (1985) *Biochem Biophys Res Com* 130:118; Dubeau et al. (1986) *Cancer Res* 46:2964; Nuovo et al. (1989) *Am J Pathol* 134:837–842; Weiss et al. (1991) *J Histochem Cytochem* 39:1237–1242). The advantage of buffered formalin is attributed to the lack of alteration in the restriction endonuclease patterns of methylation sensitive enzymes and the ability to clone the DNA. Although the target tissues consistently showed good hybridization signals when fixed in buffered formalin, tissue adherence was poor. Decreased tissue retention during hybridization may be attributed to the reduced binding capacity of overfixed tissue to charged molecules on the slide coating responsible for tissue adhesion (Wilcox, J N (1993) Fundamental principles of in situ hybridization. *J Histochem Cytochem* 41:1725–1733). Shortening the fixation time of fish and worms from 48 to 24 h in neutral buffered formalin improved the tissue morphology and consequently, the visualization of the parasite.

Attempts to use Davidson's solution as a fixative showed generally better retention on the slide but mild to moderate tissue backgrounds overwhelmed signal intensity. Davidson's solution however, had the advantage that decalcification of skeletal elements was not required making the cranial cartilages of the fish, which are preferred sites for development of the parasite, easier to section.

Archival fish and worm tissues fixed in Bouin's solution were also examined by ISH for presence of the parasite DNA. However, signals were weak or inconsistent in target tissues positive for *M. cerebralis* DNA. This result is consistent with previous findings indicating the degrading effect of the fixative on DNA integrity (see, e.g., Goelzet al., supra).

The early developmental forms of the parasite showed strong hybridization signals after the tissues were treated with 50 $\mu$g/ml proteinase K. However, the mature spores occasionally showed weak or inconsistent signals around the polar capsules. Treatments with a high concentration of proteinase K (250 $\mu$g/ml) or a combination of lysozyme (5 and 10 mg/ml) followed by low level proteinase K failed to increase the signal and also destroyed the tissue morphology. Parasite DNA present in the polar capsules may not have been adequate as target for the probe to bind to.

Post hybridization washes at 40° C. was effective in removing unhybridized probe from the tissues compared to parallel washes conducted at room temperature. However, purple precipitates indicating positive hybridization signals were observed in the gut of both fish and worms exposed and unexposed to the parasite. These precipitates were confirmed for the absence of *M. cerebralis* DNA by polymerase chain reaction test. The signal is presumably attributed to the non-specific binding of the probe to unknown cellular or enzymatic components present in the gastrointestinal tract. These nonspecific signals were partly resolved after counterstaining the tissues with Bismarck Brown Y solution.

The positive signal intensity was increased by prolonged incubation of the BCIP/NBT substrate at room temperature. Although the sensitivity of alkaline phosphatase with NBT/BCIP in filter hybridization is linear with time exposure to the substrate was limited to 6 h to eliminate nonspecific binding.

Tissue extraction followed by spore concentration have been effective for identification of mature spores of *M. cerebralis*. The presence of valves in mature spores may have protected them from this rigorous detection technique. The early developmental stages on the other hand, are destroyed with this procedure rendering them difficult or impossible to identify. By ISH, tissues with early parasitic stages including the skin epithelium and fins, or tissues with advanced spore stages such as the cranial cartilages, gill pockets, vertebral column and peripheral nerves, are not subjected to a severe digestion/concentration step. The tissues containing the target locations for the probe to bind to the parasite DNA are immediately fixed, sectioned and sequentially processed for ISH. Of particular importance from these target tissues are the amoeboid sporogonic stages that can be adequately identified by ISH but may be difficult to recognize by histology or may be missed entirely by extraction procedures.

Unlike prior art methods, the ISH protocol can detect early stages (naked sporoplasms) at the onset of the parasite invasion in fish including the epithelium of the skin, fins (caudal, ventral and dorsal), gills and buccal cavity as experimentally demonstrated in rainbow trout. In worms, a low incidence of simple multicellular developmental forms to pansporocysts and near mature triactinomyxon stages in the gut epithelium could be easily detected by ISH compared to parallel sections stained with H&E. Extraction and concentration procedures used for hardened spores, as in fish, are not useful in detecting developmental forms of *M. cerebralis* in its oligochaete host.

The most important advantage of the ISH protocol over other current methods of detecting *M. cerebralis* is its ability to permit anatomic localization of all forms of the parasite in early developmental forms or mature spore stages at low level infections. The ISH protocol we describe here may be useful as a diagnostic and research tool for investigating the complex interaction of the parasite in its two-host life cycle. The technique may also be applied for the detection of other species of Myxobolus or other myxosporean parasites such as *C. shasta* or the PKX organism. The utility of the procedure for the detection of PKX in paraffin-fixed tissues has been initiated in our laboratory. Moreover, using the appropriate primers, mixed infections caused by one or more parasites may be simultaneously detected in situ with this technique when modified accordingly. Most importantly, this diagnostic approach will enhance the detection of *M. cerebralis* in subclinically infected fish populations and in oligochaete worms to prevent the contamination of culture facilities or wild stocks with the parasite.

All publications and patents mentioned in this specification are herein incorporated by reference into the specification to the same extent as if each individual publication or patent was specifically and individually indicated to be incorporated herein by reference.

What is claimed is:

1. An isolated nucleic acid of at least about 15 nucleotides in length which selectively hybridizes to an 18S ribosomal nucleic acid of *Myxobolus cerebralis* as shown in SEQ ID NO:1.

2. The nucleic acid of claim 1, wherein the nucleic acid is at least 20 nucleotides in length.

3. The nucleic acid of claim 1, wherein the nucleic acid is a ribonucleic acid.

4. The nucleic acid of claim 1, which is a nucleic acid selected from the group consisting of:
5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3'(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:1 1), and
5'-CAATTTGCAACAAGTAAGAGTTTTATC-3(SEQ ID NO:12).

5. The nucleic acid of claim 4, which is a nucleic acid selected from the group consisting of
5'-GCCCTATTAACTAGTTGGTAGTATAGAAGC-3'(SEQ ID NO:6), and
5'-GGCACACTACTCCAACACTGAATTTG-3'(SEQ ID NO:7).

6. The nucleic acid of claim 4, which is a nucleic acid selected from the group consisting of:
5'-GCATTGGTTTACGCTGATGTAGCGA-3'(SEQ ID NO:4) and
5'-GGCACACTACTCCAACACTGAATTTG-3'(SEQ ID NO:7).

7. An isolated nucleic acid of at least about 15 nucleotides in length which selectively hybridizes to an 18S ribosomal nucleic acid of *Myxobolus insidiosus* as shown in SEQ ID NO:2.

8. An isolated nucleic acid of at least about 15 nucleotides in length which selectively hybridizes to an 18S ribosomal nucleic acid of *Myxobolus squamalis* as shown in SEQ ID NO:3.

9. A method of detecting Myxobolus spp. nucleic acids in an aquatic sample, the method comprising the steps of:
contacting the aquatic sample with a nucleic acid probe comprising a nucleic acid segment capable of selectively hybridizing to SEQ ID NO:1, SEQ ID NO:2, or SEQ ID NO:3 to form a hybridization complex; and
detecting the hybridization complexes as an indication of the presence of Myxobolus spp. in the sample.

10. The method of claim 9, further comprising the step of amplifying the Myxobolus spp. nucleic acids in the sample.

11. The method of claim 10, wherein the step of amplification is carried out using the polymerase chain reaction.

12. The method of claim 11, wherein the step of amplification is carried out using a primer which selectively hybridizes to the same nucleic acid sequence of an *Myxobolus cerebralis* 18S ribosomal nucleic acid as an oligonucleotide selected from the group consisting of:
5'-GCATTGGTTTACGCTGATGTAGCGA-3'(SEQ ID NO:4)
5'-GAATCGCCGAAACAATCATCGAGCTA-3'(SEQ ID NO:5)
5'-GCCCTATTAACTAGTTGGTAGTATAGAAGC-3'(SEQ ID NO:6)
5'-GGCACACTACTCCAACACTGAATTTG-3'(SEQ ID NO:7)
5'-GGCAGCGTTAAAACTGTCTCACG-3'(SEQ ID NO:8)
5'-ACCGCGGCTGCTGGCACCAG-3'(SEQ ID NO:9)
5'-AGCGAGTAAGGTGAATCTAGATAAC-3'(SEQ ID NO:10)
5'-CTTAAATTACGTCCATTCCAAGCTG-3'(SEQ ID NO:11), and
5'-CAATTTGCAACAAGTAAGAGTTTTATC-3 (SEQ ID NO:12).

13. The method of claim 11, wherein the step of amplification comprises selectively hybridizing primers to a nucleic acid sequence; wherein said nucleic acid sequence selectively hybridizes to SEQ ID NO:4 or SEQ ID NO:5; and wherein said amplification forms a first amplified segment.

14. The method of claim 13, wherein a subsequence of the first amplified segment is amplified with primers which selectively hybridize to the same nucleic acid sequence as SEQ ID NO:6 or SEQ ID NO:7.

15. The method of claim 11, wherein the step of amplification comprises selectively hybridizing primers to a nucleic acid sequence; wherein said nucleic acid sequence selectively hybridizes to SEQ ID NO:8 or SEQ ID NO:9; and wherein said amplification forms a first amplified segment.

16. The method of claim 15, wherein a subsequence of the first amplified segment is amplified with primers which selectively hybridize to the same nucleic acid sequence as SEQ ID NO:10 or SEQ ID NO:11.

17. The method of claim 11, wherein the step of amplification comprises selectively hybridizing primers to a nucleic acid sequence; wherein said nucleic acid sequence selectively hybridizes to SEQ ID NO:4 or SEQ ID NO:7.

18. The method of claim 9, wherein the Myxobolus spp. nucleic acid is a ribonucleic acid.

19. The method of claim 9, wherein the aquatic sample is from a salmonid fish.

20. The method of claim 9, wherein the aquatic sample is from a salmonid fish.

21. The method of claim 9, wherein the nucleic acid is contacted with the aquatic sample in situ.

22. The method of claim 21, wherein the sample is treated with proteinase K at a concentration of between about 25 $\mu$g/ml to about 50 $\mu$g/ml.

23. The method of claim 21, wherein the concentration of the nucleic acid probe in a hybridization solution is between about 10 fmole/$\mu$l and about 20 fmole/$\mu$l.

24. The method of claim 21, wherein the nucleic acid probe and the nucleic acids in the sample are denatured simultaneously.

25. The method of claim 21, wherein the aquatic sample is from an oligochaete worm.

26. The method of claim 21, wherein the aquatic sample is from a salmonid fish.

27. The method of claim 21, wherein the probe is prepared by amplification of *M. cerebralis* nucleic acids using primers which selectively hybridize to the same nucleic acid sequence as SEQ ID NO:4, SEQ ID NO:5, or SEQ ID NO:7.

28. A diagnostic kit for use in determining the presence of *Myxobolus cerebralis* in an aquatic sample, which kit comprises a container having a nucleic acid comprising a nucleic acid segment capable of selectively hybridizing to an 18S ribosomal nucleic acid of *Myxobolus cerebralis* as shown in SEQ ID NO:1.

29. The diagnostic kit of claim 28, wherein the nucleic acid comprising the nucleic acid segment selectively hybridizes to the same nucleic acid sequence of a *Myxobolus cerebralis* 18S ribosomal nucleic acid as an oligonucleotide selected from the group consisting of:

5'-GCATTGGTTTACGCTGATGTAGCGA-3'(SEQ ID NO:4)

5'-GAATCGCCGAAACAATCATCGAGCTA-3'(SEQ ID NO:5)

5'-GCCCTATTAACTAGTTGGTAGTATAGAAGC-3'(SEQ ID NO:6)

5'-GGCACACTACTCCAACACTGAATTTG-3'(SEQ ID NO:7)

5'-GGCAGCGTTAAAACTGTCTCACG-3'(SEQ ID NO:8)

5'-ACCGCGGCTGCTGGCACCAG-3'(SEQ ID NO:9)

5'-AGCGAGTAAGGTGAATCTAGATAAC-3'(SEQ ID NO:10)

5'-CTTAAATTACGTCCATTCCAAGCTG-3'(SEQ ID NO:11), and

5'-CAATTTGCAACAAGTAAGAGTTTTATC-3 (SEQ ID NO:12).

30. The diagnostic kit of claim 28, wherein the container comprises nucleic acids comprising nucleic acid segments that selectively hybridize to the same nucleic acid sequence of a *Myxobolus cerebralis* 18S ribosmal nucleic acid as SEQ ID NO:4 and SEQ ID NO:7.

31. The diagnostic kit of claim 28, wherein the container comprises nucleic acids comprising nucleic acid seqments that selectiviely hybridize to the same nucleic acid sequence of a *Myxobolus cerebralis* 18S ribosmal nucleic acid as SEQ ID NO:4, SEQ ID NO:5, SEQ ID NO:6, and SEQ ID NO:7.

* * * * *